US00PP13898P39

(12) United States Plant Patent
Rigney

(10) Patent No.: US PP13,898 P3
(45) Date of Patent: Jun. 17, 2003

(54) LAVATERA PLANT NAMED 'RED RUM'

(76) Inventor: Ken Rigney, 137B King George's Ave. Regents Park, Southhampton, Hampshire S015 4LE (GB)

( * ) Notice: Subject to any disclaimer, the term of this patent is extended or adjusted under 35 U.S.C. 154(b) by 14 days.

(21) Appl. No.: 09/907,023

(22) Filed: Jul. 17, 2001

(65) Prior Publication Data

US 2003/0019002 P1 Jan. 23, 2003

(51) Int. Cl.[7] ..... A01H 5/00
(52) U.S. Cl. ..... Plt./226
(58) Field of Search ..... Plt./263, 226, 257

(56) References Cited

PUBLICATIONS

Huxley, ed., 1992, The New Royal Horticultural Society Dictionary of Gardening, MacMillan Press Ltd., London, pp. 25–26, vol. 3, L–Q, 1992.*

* cited by examiner

*Primary Examiner*—Howard J. Locker

(57) ABSTRACT

A new cultivar of Lavatera named 'Red Rum' that is characterized by a compact habit, dark stems and red flowers in terminal clusters. In combination these traits set 'Red Rum' apart from all other existing varieties of Lavatera known to the inventor.

2 Drawing Sheets

Botanical classification: *Lavatera thuringiaca.*
Variety denomination: 'Red Rum'.

BACKGROUND OF THE INVENTION

The present invention relates to a new and distinct cultivar of Tree Mallow, a perennial shrub with a compact habit, grown for use as an ornamental landscape and accent plant. The new cultivar is known botanically as a *Lavatera thuringiaca* and will be referred to hereinafter by the cultivar name 'Red Rum'.

In 1996, a plant was found by the inventor in a cultivated garden area of Southampton, United Kingdom. The garden contained plants of Lavatera 'Bredon Springs' (unpatented) and Lavatera 'Burgundy Wine' (unpatented). It is believed that 'Burgundy Wine' and 'Bredon Springs' are the parents. However, the exact parents are unknown.

The traits that make 'Red Rum' unique are, very dark almost black stems, a compact growth habit, the shape and color of the flowers as well as their arrangement in terminal clusters. The flowers of 'Red Rum' are arranged along the stem in tighter clusters in comparison to typical Lavateras. The closest comparision plants are 'Bredon Springs' and 'Burgandy Wine'. 'Red rum' is distinguishable from 'Bredon Springs' by a compact habit. 'Red Rum' is shorter than 'Bredon Springs' and about the same size as 'Burgundy Wine'. 'Red Rum' differs from both 'Burgundy Wine' and 'Bredon Springs' in its darker flower color and stem color. The flower color of 'Red Rum' is nearer to red than any other Lavatera known to the inventor.

'Red Rum' was first asexually propagated by the inventor in 1996 in Southampton, United Kingdom using stem cuttings. Since that time, under careful observation, the distinguishing characteristics have been determined stable and uniform in successive generations.

SUMMARY OF THE INVENTION

The following represent the distinguishing characteristics of the new Lavatera cultivar 'Red Rum'. In combination these traits set 'Red Rum' apart from all other existing varieties of Lavatera known to the inventor. 'Red Rum' has not been tested under all possible conditions and phenotypic differences may be observed with variations in environmental, climatic, and cultural conditions, however, without any variance in genotype.

1. Lavatera 'Red Rum' exhibits red flowers along the stems and in terminal clusters.

2. Lavatera 'Red Rum' exhibits a compact growth habit.

3. Lavatera 'Red Rum' exhibits dark, almost black stems.

4. Lavatera 'Red Rum' is 150 cm. in height and 150 cm. in width at maturity.

BRIEF DESCRIPTION OF THE DRAWINGS

The accompanying color photographs illustrate the distinguishing traits of Lavatera 'Red Rum'. The plant in the photographs is twelve months and was grown outdoors in Arroyo Grande, Calif. in a five-gallon container.

The photograph on sheet 1 illustrates the entire plant in a five-gallon container from a side perspective.

The photograph on sheet 2 is a close-up view of the flowers and terminal cluster of buds. All photographs are taken using conventional techniques and although foliage colors may appear different from actual colors due to light reflectance, they are as accurate as possible by conventional photography.

BOTANICAL DESCRIPTION OF THE PLANT

The following is a detailed description of the Lavatera cultivar named 'Red Rum'. Data was collected in Arroyo Grande, Calif. from twelve-month plants grown outdoors in five-gallon containers. Color determinations are in accordance with The Royal Horticultural Society Colour Chart except where general color terms of ordinary dictionary significance are used. 'Red Rum' prefers full sun, regular watering and well drained moderately fertile soil.

Botanical classification: *Lavatera thuringiaca* 'Red Rum'.
Common name: Tree Mallow.
Use: Ornamental landscape shrub and accent plant.
Parentage: The parents of 'Red Rum' are unknown.
Vigor: Vigorous.
Growth habit: Compact.
Plant shape: Vase-shaped.
Height: 150 cm. in height.
Width: 150 cm. in width.
Hardiness: Hardy to minus 8.5° Centigrade, tolerant to frost.
Propagation: Cuttings.
Root system: Fine and fibrous.
Cultural requirements: Plant in full sun and well-drained soils.
Type: Perennial.
Time to initiate roots: Requires 14–28 days to produce roots on an initial cutting.
Crop time: Requires 9 months to produce a five-gallon container from a rooted cutting.
Seasonal interest: Flowers in summer.
Stem:
*Branching habit.*—Upright branching.
*Stem diameter.*—0.75 cm.
*Stem length.*—90 cm. in length.
*Internode length.*—4–6 cm. between nodes.
*Shape.*—Cylindrical.
*Surface.*—Tufted with long soft hairs.
*Branch color.*—200B.
Foliage:
*Leaf arrangement.*—Alternate.
*Leaf division.*—Simple.
*Leaf margin.*—Crenate.
*Leaf shape.*—Tri-lobed.
*Leaf base.*—Cordate.
*Leaf apex.*—Acute.
*Leaf venation.*—Palmate with the veins on the adaxial surface depressed and the veins on the abaxial surface protruding.
*Vein color* (*adaxial surface*).—189A.
*Vein color* (*abaxial surface*).—Central vein is 187A and all others are 191C.
*Leaf surface* (*adaxial*).—Pubescent.
*Leaf surface* (*abaxial*).—Mostly pubescent with veins lanate.
*Leaf texture.*—Velutinous.
*Leaf attachment.*—Long-petiolate.
*Petiole dimensions.*—5.5 cm. in length and 3 mm. in width.
*Petiole color.*—187A.
*Petiole surface.*—Flocculent.
*Stipules.*—Absent.
*Leaf length.*—8.5 cm. in length.
*Leaf width.*—7.0 cm. in width.
*Leaf color* (*adaxial surface*).—146A.
*Leaf color* (*abaxial surface*).—191A.
*Foliar fragrance.*—Absent.
Flower:
*Sexuality.*—Bisexual and synoecious.
*Flower arrangement.*—Alternate and clustered.
*Form.*—Raceme.
*Inflorescence.*—Indeterminate.
*Lastingness.*—3–5 days.
*Dimensions of panicle.*—17 cm. in length and 7 cm. in width.
*Quantity of flowers per stem.*—Approximately 20–25 flowers per stem.
*Shape of flower.*—Rotate and forming a shallow cupule.
*Flower markings.*—Darker red veins running length of petals.
*Symmetry.*—Symmetrical.
*Dimensions of flower.*—1.75 cm. in height and 6.5 cm. in diameter.
*Aspect.*—Facing outward.
*Color of flower petal.*—A combination of overall color effect 72A and darker veins of 71A.
*Petals.*—Five in number.
*Petal shape and arrangement.*—Shape is obdeltoid with petals overlapping.
*Petal length.*—3.75 cm in length.
*Petal width.*—2.75 cm in width.
*Unfused or fused.*—Petals are unfused in relationship to one another but adnate to the stamen column.
*Petal surface.*—Furrows along dark veins.
*Petal margin.*—Entire.
*Bud color.*—72A.
*Bud shape.*—Oval.
*Bud dimensions.*—1.75 cm. in length and 1.25 cm. in diameter.
*Persistent or self-cleaning.*—Self-cleaning.
*Shape of calyx.*—Campanulate.
*Color of calyx.*—144A.
*Dimensions of calyx.*—1.5 mm. in diameter and 1.75 mm. in length.
*Shape of epicalyx.*—Campanulate.
*Number of sepals in epicalyx.*—Three sepals in epicalyx.
*Surface of calyx and epicalyx* (*adaxial and abaxial*).—Lanate.
*Number of sepals in calyx.*—Five sepals in calyx.
*Fused or unfused.*—Sepals are basally fused in calyx and epicalyx.
*Sepal color upper surface.*—191A.
*Sepal color lower surface.*—191A.
*Dimensions of sepal.*—0.50 mm. in width and 1.75 mm. in length.
*Blooming period.*—April to May.
*Peduncle* (*primary*).—17 to 23 cm. in length and 3 mm. in diameter.
*Peduncle* (*secondary*).—4 cm. in length and less than 1 mm. in width.
*Color of peduncle.*—144B.
*Surface of peduncle.*—Setose and fluted.
*Fragrance.*—Absent.
Reproductive organs:
*Stamens.*—Monadelphous.
*Color of stamens.*—71B.
*Dimensions of stamen filament.*—5 mm. in length and less than 0.25 mm. in diameter.
*Stamen filaments.*—Intricate.
*Stamen column.*—Stamens and corolla are fused into a single unit called the stamen column.
*Color of stamen column.*—71B.
*Dimensions of stamen column.*—1.50 cm. in length and 2.75 mm. in diameter.
*Surface of stamen column.*—Fluted and lanate.
*Shape of anther.*—Crescent-shaped pouch.
*Dimensions of anther.*—1 mm. in length and 0.50 mm. in width.
*Anther color.*—72D.
*Pollen color.*—156A.

*Pistil.*—Not observable to the naked eye. The pistil is surrounded by the stamen column.

*Dimensions of pistil.*—Approximately 1.75 cm. in length and 2 mm. in width.

*Stigma.*—Exserted.

*Stigma color.*—71B.

*Dimensions of stigma.*—0.25 cm. in length and 1 mm. in width.

*Style color.*—Not observable to the naked eye.

*Style.*—Extends upward through stamen column.

*Style dimensions.*—1 cm. in length and 1 mm. in width.

*Ovary position.*—Superior.

*Ovary color.*—155B.

*Ovary dimensions.*—6 mm. in diameter and 3 mm. in height.

Seed: Seed production has not been observed.

I claim:

1. A new and distinct variety of Lavatera plant named 'Red Rum', as described and illustrated.

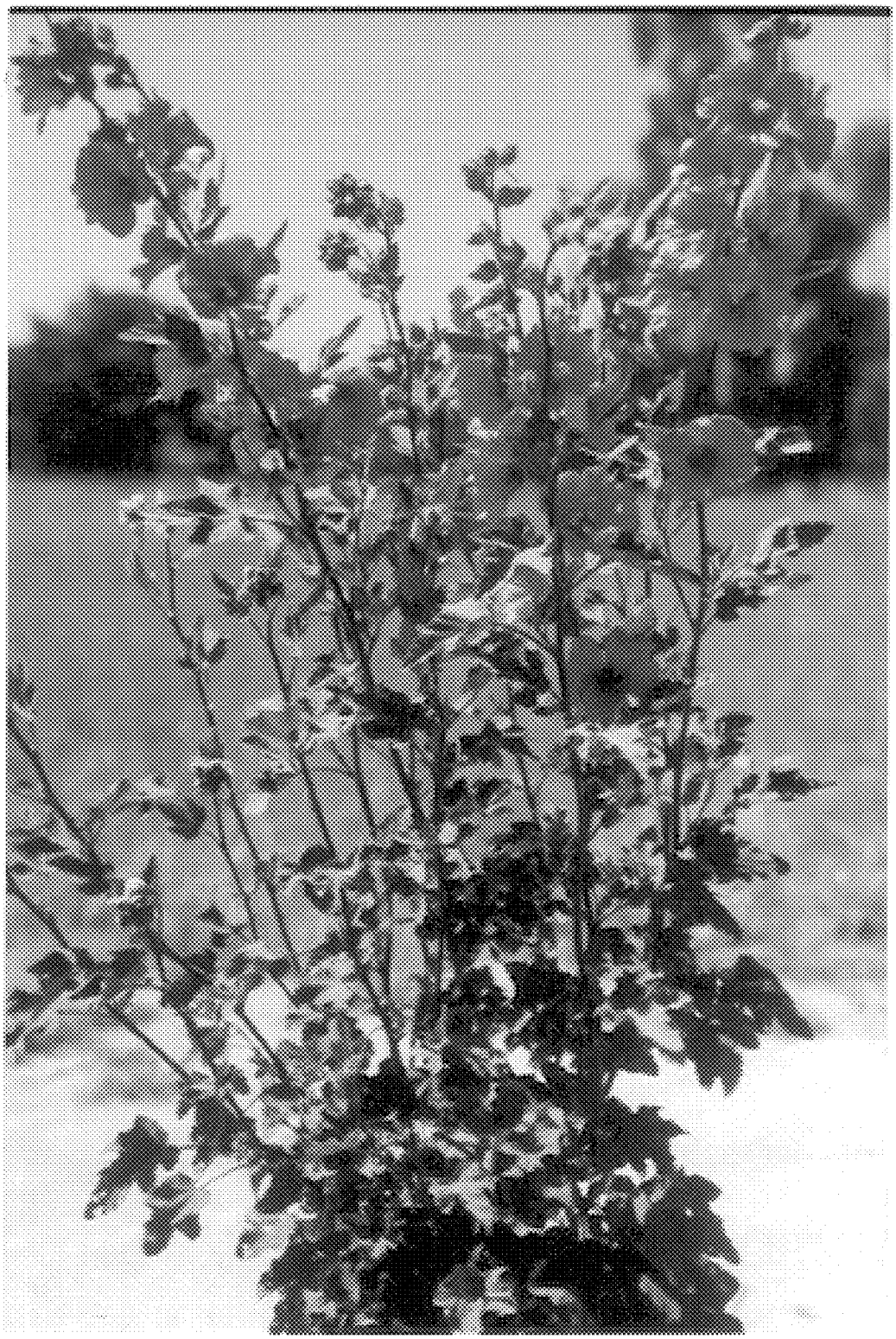

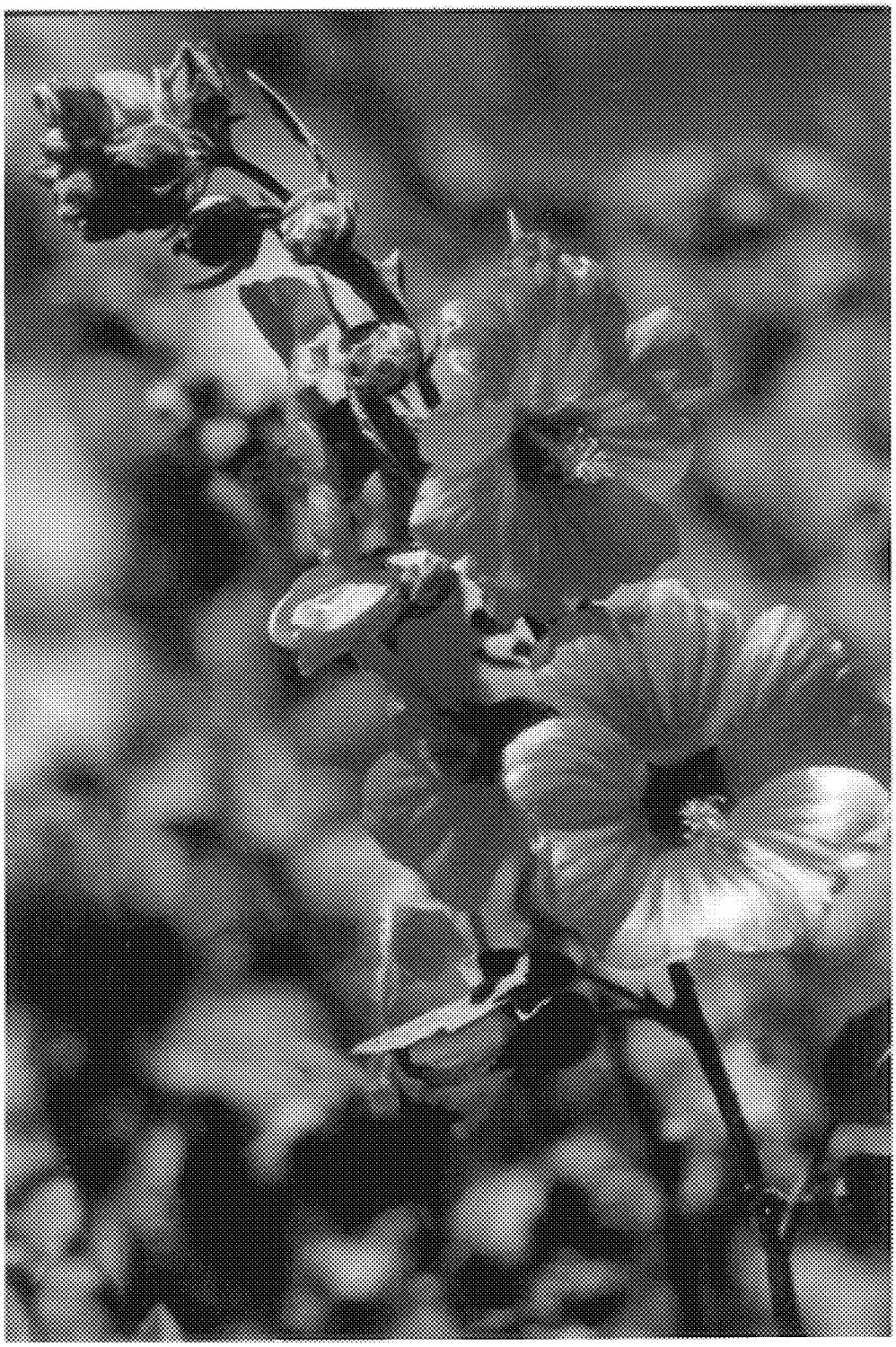

* * * * *